(12) United States Patent
Hamatake

(10) Patent No.: US 9,456,760 B2
(45) Date of Patent: Oct. 4, 2016

(54) CLOSED CATHETER TIP INCLUDING ELECTRICALLY CONDUCTIVE PATHWAY

(71) Applicant: C. R. Bard, Inc., Murray Hill, NJ (US)

(72) Inventor: Bret Hamatake, Grantsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 156 days.

(21) Appl. No.: 14/209,600

(22) Filed: Mar. 13, 2014

(65) Prior Publication Data

US 2014/0275918 A1    Sep. 18, 2014

Related U.S. Application Data

(60) Provisional application No. 61/784,625, filed on Mar. 14, 2013.

(51) Int. Cl.
| | | |
|---|---|---|
| *A61B 5/042* | (2006.01) | |
| *A61B 5/00* | (2006.01) | |
| *A61L 29/06* | (2006.01) | |
| *A61L 29/14* | (2006.01) | |

(52) U.S. Cl.
CPC .............. *A61B 5/042* (2013.01); *A61B 5/6852* (2013.01); *A61L 29/06* (2013.01); *A61L 29/146* (2013.01); *A61B 2562/0209* (2013.01)

(58) Field of Classification Search
CPC .............................. A61B 5/042; A61B 5/0422
See application file for complete search history.

(56) References Cited

U.S. PATENT DOCUMENTS

| | | |
|---|---|---|
| 3,416,533 A | 12/1968 | Fisher et al. |
| 3,769,984 A | 11/1973 | Muench |
| 4,329,993 A | 5/1982 | Lieber et al. |
| 4,592,372 A | 6/1986 | Beranek |
| 5,005,587 A | 4/1991 | Scott |

(Continued)

FOREIGN PATENT DOCUMENTS

| | | |
|---|---|---|
| WO | 9424931 A1 | 11/1994 |
| WO | 2004065098 A1 | 8/2004 |

(Continued)

OTHER PUBLICATIONS

PCT/US14/26149 filed Mar. 13, 2014 International Search Report and Written Opinion dated Jul. 28, 2014.

(Continued)

*Primary Examiner* — Lee S Cohen
(74) *Attorney, Agent, or Firm* — Rutan & Tucker, LLP

(57) ABSTRACT

A closed-ended catheter assembly that includes an electrically conductive pathway is disclosed. The conductive pathway enables electrical signals, such as ECG signals produced by a patient's heart, to pass through the closed-ended tip of the indwelling catheter while still preventing unintended fluid flow. In one embodiment, therefore, a catheter assembly is disclosed and comprises an elongate catheter tube including a closed distal end. The catheter tube defines at least one lumen and includes a valve defined in the catheter tube that is configured to selectively enable fluids to pass therethrough. The catheter tube includes a conductive element that provides an electrically conductive pathway between the at least one lumen and an exterior portion of the catheter. The conductive element includes a porous material extending between the at least one lumen and the exterior portion of the catheter, the porous material being transmissive to electrical signals and non-permeable to blood.

7 Claims, 9 Drawing Sheets

(56) References Cited

U.S. PATENT DOCUMENTS

| | | |
|---|---|---|
| 5,281,218 A | 1/1994 | Imran |
| 5,348,554 A | 9/1994 | Imran et al. |
| 5,433,742 A | 7/1995 | Willis |
| 5,643,197 A * | 7/1997 | Brucker ............ A61B 18/1492 604/164.08 |
| 5,772,642 A | 6/1998 | Ciamacco, Jr. et al. |
| 5,888,577 A | 3/1999 | Griffin, III et al. |
| 5,913,856 A | 6/1999 | Chia et al. |
| 6,017,338 A * | 1/2000 | Brucker ............ A61B 18/1492 606/122 |
| 6,032,061 A | 2/2000 | Koblish |
| 6,440,488 B2 | 8/2002 | Griffin, III et al. |
| 6,475,184 B1 | 11/2002 | Wang et al. |
| 6,562,021 B1 | 5/2003 | Derbin et al. |
| 6,912,423 B2 | 6/2005 | Ley et al. |
| 7,231,259 B2 | 6/2007 | Jenney et al. |
| 7,559,137 B2 | 7/2009 | Beer et al. |
| 7,629,015 B2 | 12/2009 | Anderson et al. |
| 7,766,907 B2 | 8/2010 | Dando et al. |
| 8,075,969 B2 | 12/2011 | Anderson et al. |
| 8,147,486 B2 | 4/2012 | Honour et al. |
| 8,442,653 B2 | 5/2013 | Gill |
| 8,543,222 B1 | 9/2013 | Sochor |
| 8,620,455 B2 | 12/2013 | Alexander et al. |
| 2006/0142652 A1 | 6/2006 | Keenan |
| 2008/0097429 A1 | 4/2008 | McClurken |
| 2009/0276020 A1 | 11/2009 | Nee et al. |
| 2010/0022950 A1 | 1/2010 | Anderson et al. |
| 2010/0222664 A1 | 9/2010 | Lemon et al. |
| 2010/0228202 A1 | 9/2010 | O'Dea et al. |
| 2010/0305673 A1 | 12/2010 | Jolly et al. |
| 2015/0182168 A1 | 7/2015 | Draper et al. |

FOREIGN PATENT DOCUMENTS

| | | |
|---|---|---|
| WO | 2011005165 A1 | 1/2011 |
| WO | 2014160247 A1 | 10/2014 |
| WO | 2015/138876 A1 | 9/2015 |

OTHER PUBLICATIONS

PCT/US2015/020415 filed Mar. 13, 2015 Search Report dated Jun. 29, 2015.

* cited by examiner

CLOSED CATHETER TIP INCLUDING ELECTRICALLY CONDUCTIVE PATHWAY

CROSS-REFERENCE TO RELATED APPLICATIONS

This application claims the benefit of the U.S. Provisional Patent Application No. 61/784,625, filed Mar. 14, 2013, and titled "Closed Catheter Tip Including Electrically Conductive Pathway," which is incorporated herein by reference in its entirety.

BRIEF SUMMARY

Briefly summarized, embodiments of the present invention are directed to a generally closed-ended catheter assembly that includes an electrically conductive pathway. The conductive pathway enables electrical signals, such as ECG signals produced by signal generating nodes of the patient's heart, to pass through the closed-ended tip of the indwelling catheter while still preventing unintended fluid flow. Such catheter assemblies are suitable for use with ECG signal monitoring devices, for instance.

In one embodiment, therefore, a catheter assembly for placement in a body of a patient is disclosed and comprises an elongate catheter tube including a closed distal end. The catheter tube defines at least one lumen and includes a valve defined in the catheter tube that is configured to selectively enable fluids to pass therethrough. The catheter tube includes a conductive element that provides an electrically conductive pathway between the at least one lumen and an exterior portion of the catheter. The conductive element includes a porous material extending between the at least one lumen and the exterior portion of the catheter, the porous material being permeable to electrical signals and non-permeable to blood.

These and other features of the present disclosure will become more fully apparent from the following description and appended claims, or may be learned by the practice of the disclosure as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to catheters and other tubular devices for use in establishing access to an internal portion of a patient's body. In particular, present embodiments are directed to catheters including generally closed distal tips and a slit valve or other opening proximate thereto in order to selectively enable fluid passage through the catheter. In accordance with one embodiment, a distal portion of the closed-ended catheter tip includes an electrically conductive pathway that enables electrical signals, such as ECG signals produced by signal generating nodes of the patient's heart, to pass through the closed-ended tip of the indwelling catheter tube while still preventing unintended fluid flow. In this way, such ECG signals may be conveyed or passed (also referred to herein as "transmitted") through the catheter to an ECG signal monitoring device operably connected to a proximal portion of the catheter residing outside of the body. Again, note that transmission of the ECG signals occurs even though the distal tip of the catheter desirably remains closed to typical fluid flow. Further details regarding one example of an ECG signal monitoring device can be found in U.S. Patent Publication No. 2011/0015533, filed Sep. 29, 2010, and entitled "Stylets for use with Apparatus for Intravascular Placement of a Catheter," which is incorporated herein by reference in its entirety.

Figure 1:
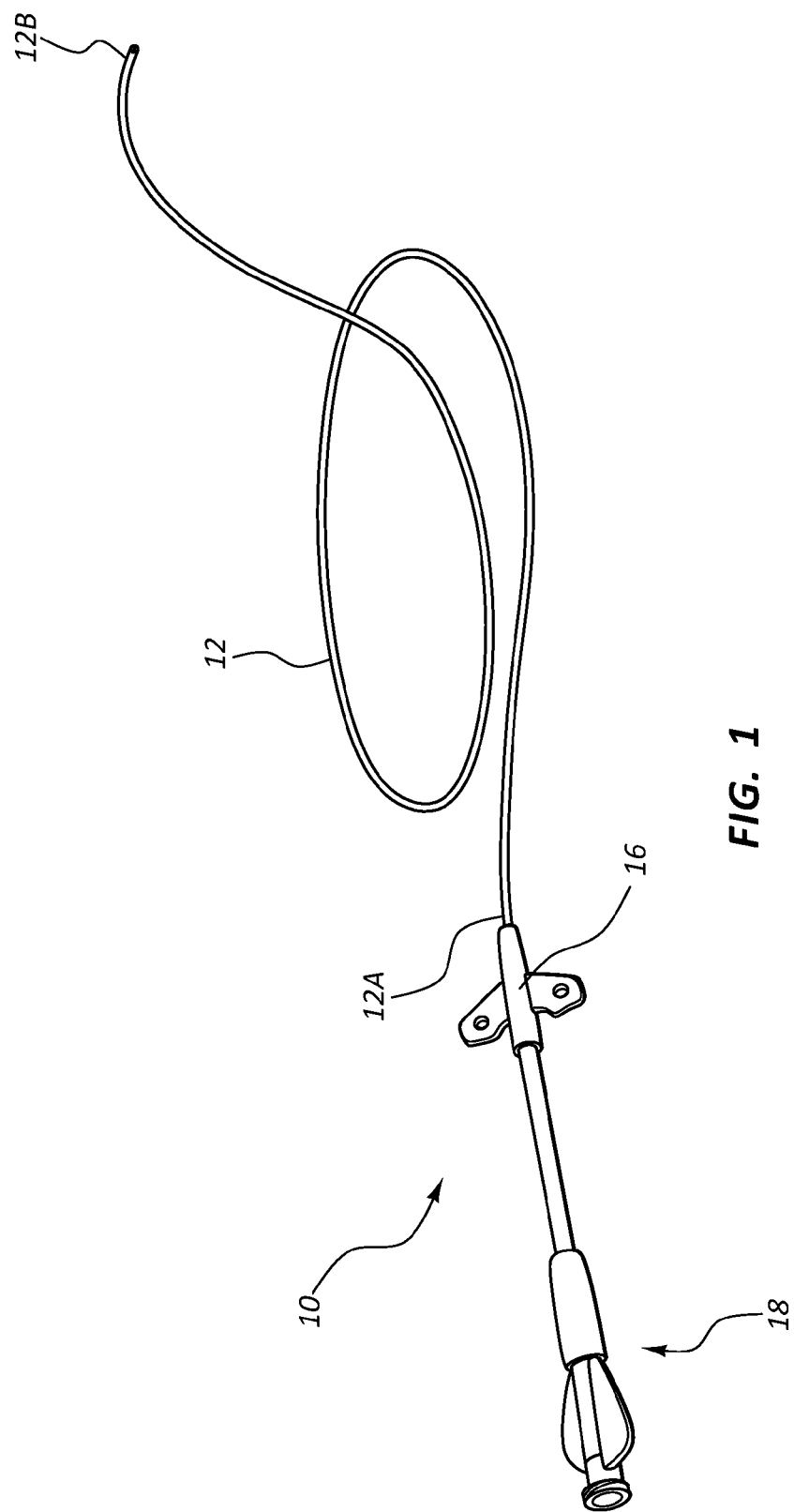
FIG. 1 is a perspective view of a catheter assembly according to one embodiment.

FIG. 1 shows a closed-ended catheter assembly ("catheter") 10 according to one embodiment, as an example device wherein embodiments described herein may be practiced. In detail, the catheter 10 is a GROSHONG® catheter manufactured by C.R. Bard, Inc., Murray Hill, N.J., and includes an elongate catheter tube 12 defining a proximal end 12A and a closed distal end 12B. A slit valve 22 (FIG. 2) is included proximate the distal end 12B of the catheter tube 12. The catheter 10 here includes a single lumen 14 (FIG. 2), though in other embodiments more than one lumen can be included. An extension leg 18 is operably attached to the proximal end 12A of the catheter tube 12 via a bifurcation 16. A distal plug 20 is inserted into the open distal end 12B of the catheter tube 12 during manufacture to close the distal end. In one embodiment, the catheter tube 12 and plug 20 include silicone, though other thermoset, thermoplastic, and other suitable materials can be used for these components. The catheter 10 described herein is configured for insertion into a blood-filled vasculature of the patient, though catheters can be used for other functions as well. Note that a variety of catheter types, brands, sizes, included slit or other valves, etc., can benefit from the principles described herein. In addition to a distal plug, other closure schemes for closing the distal end of the catheter tube are possible.

Figure 2:
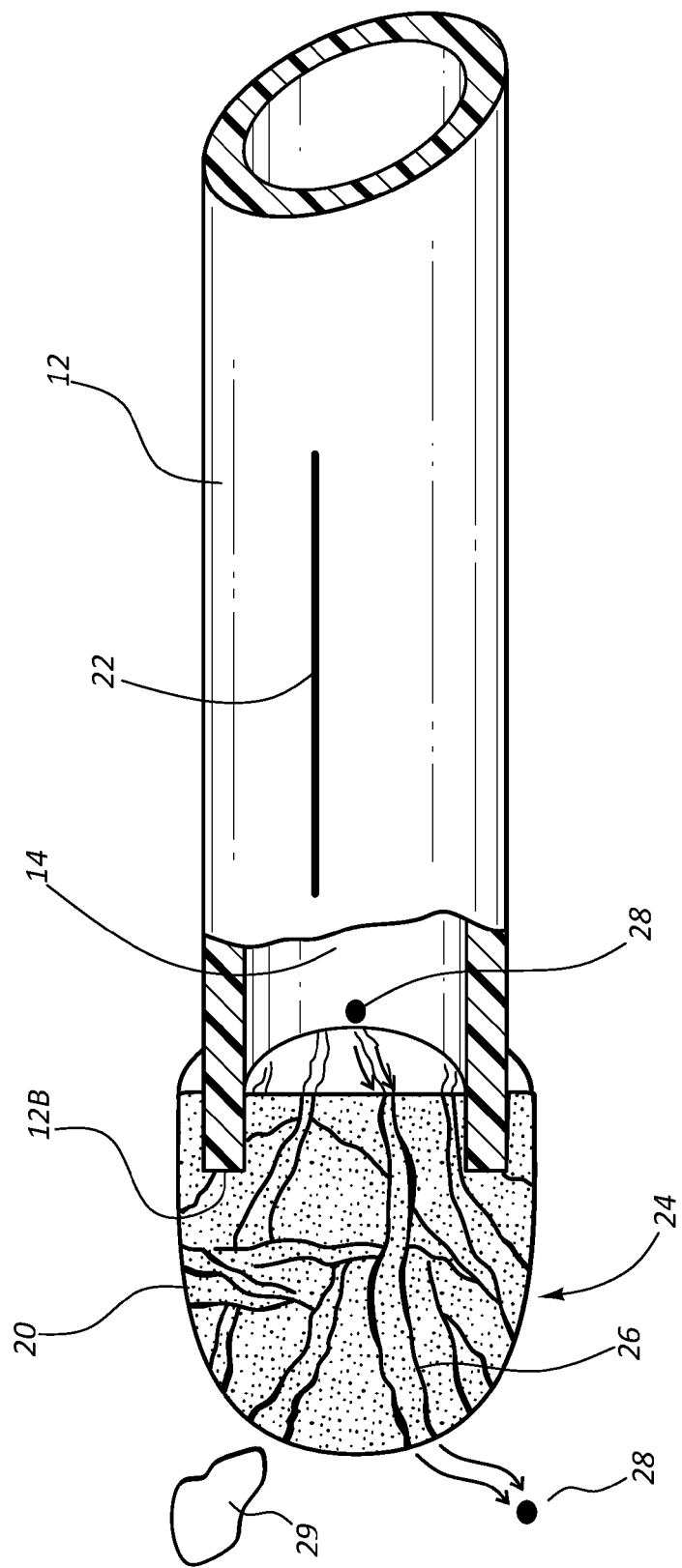
FIG. 2 is a cross sectional view of a distal portion of a catheter tube according to one embodiment.

FIG. 2 shows a distal portion of the catheter 10 including the catheter tube 12 and a slit valve 22 defined through the wall of the catheter tube such that it is selectively openable to enable fluid transfer to/from the lumen 14 when a sufficient pressure differential exists across the valve. Note that other slit valves and valve configurations can be employed with the catheter tube 12. The distal plug 20 is shown attached to the distal end 12B of the catheter tube 12 so as to close the tube and define a distal end of the tube and the lumen 14 defined thereby.

In the present embodiment depicted in FIG. 2, the catheter 10 further includes a conductive element 24 that provides an electrically conductive pathway for enabling electrical signals to pass between the lumen 14 and the exterior of the catheter 10. As shown, the conductive element 24 of the present embodiment includes the distal plug 20 that closes the lumen 14. Specifically, the distal plug 20 includes a material including micron-sized micropore (microporous) channels 26 that extend in an interconnected, network-like manner through the plug material. The size of the micropores 26 enables the passage of ions 28, and thus electrical signal passage, between the blood within the vasculature in which the indwelling catheter 10 is disposed and the interior of the lumen 14 where a conductive stylet (FIG. 3) or conductive liquid such as saline is present. The micropore channels 26, however, are small enough to prevent the passage of blood cells 29 therethrough, thus preventing fluid leakage through the plug 20. Note that the sizes of the ions 28 and blood cells 29 are not drawn to scale relative the catheter tube 12 in FIG. 2.

In one embodiment, suitable polymeric materials are used to form the micropore plug material. As mentioned, characteristics of a plug material suitable for the above purpose include the ability to enable electrical signals to pass while preventing fluid flow therethrough. As discussed, this is achieved in the present embodiment by forming the plug from a material that includes suitably small, interconnected or discrete channels through the material, porous material, sponge-like material, etc. The materials mentioned herein are therefore not to be considered limiting.

In another embodiment, a silicone foam material can be used to form the plug 20 and thus define the conductive element 24. The silicone foam facilitates ease of attachment to the distal end 12B of the catheter tube in the case where the catheter tube includes silicone as well. So configured, the foam material of the plug 20 acts like a sponge and provides a fluid-filled conductive pathway between the exterior surface of the plug 20 and the interior lumen 14. Conductive saline present in the catheter tube lumen 14 can infiltrate into foam material of the plug 20 to provide the conductive pathway between the lumen and the catheter tube exterior. One supplier of such material is Filtrona Porous Technologies, Colonial Heights, Va.

In yet another embodiment, a salt solution or other conductive fluid can be impregnated into or absorbed by the foam or other suitable material of the plug 20 prior to insertion of the catheter 10 into the patient vasculature to enhance electrical conductivity.

As with the other embodiments described herein, the conductive element 24 enables electrical signals, such as ECG signals from the patient's heart, to pass through the indwelling catheter tube 12, via the conductive element, into the catheter tube lumen 14, thus forming the aforementioned conductive pathway. These signals can then pass proximally up through the catheter tube 12 and extension leg 18 to the proximal end of the catheter 10 via conductive solution disposed in the lumen, a stylet disposed in the lumen, or by another suitable configuration. These signals can then be received by an ECG signal monitoring device, as discussed. A suitable connector or interface can be employed to operably connect the stylet, conductive solution, etc., to the signal monitoring device, such as a luer connector securable to the extension leg connector that attaches to the stylet.

Note that the conductive elements discussed herein can include one, two, or more components that cooperate to provide an electrically conductive pathway through the catheter.

Figure 3:
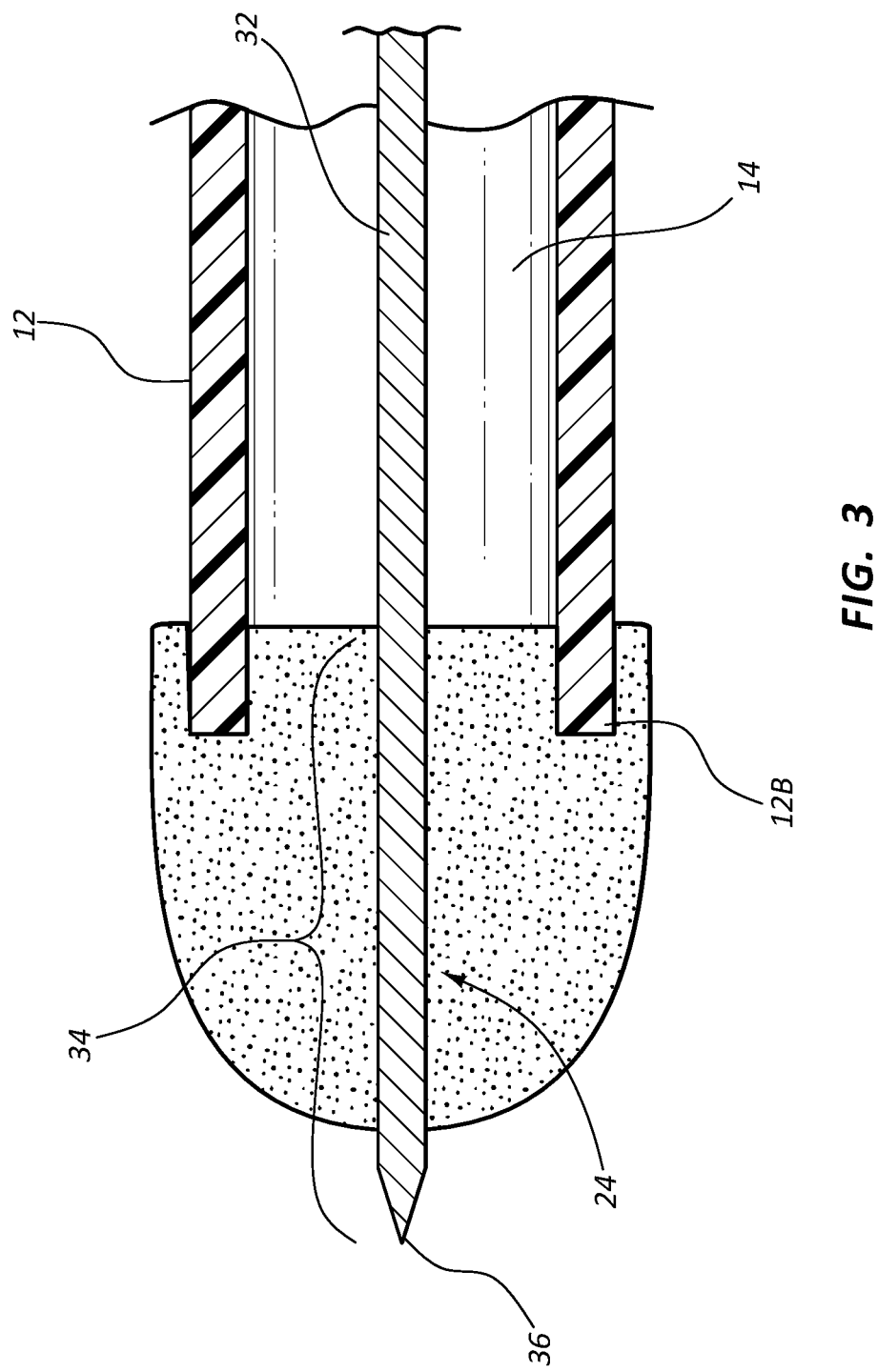
FIG. 3 is a cross sectional view of a distal portion of a catheter tube according to one embodiment.

FIG. 3 shows a distal portion of the catheter 10 according to one embodiment, including another example of the conductive element 24 for providing an electrically conductive pathway through the catheter tube. As shown, a distal portion 34 of an electrically conductive stylet 32 is inserted into the lumen 14 of the catheter tube 12 and is distally advanced sufficient to cause a sharpened distal tip 36 thereof to pierce and extend from a compliant distal plug 30 of the catheter tube. This establishes an electrically conductive pathway from the lumen 14 interior to the exterior of the catheter 10. Once the conductive pathway is no longer needed, the stylet 32 can be pulled proximally by a user such that the stylet distal portion 34 and tip 36 are disengaged from the plug 30. The compliant plug 30 includes silicone or other suitable self-sealing material such that the hole created by the stylet piercing seals to prevent fluid passage therethrough. In one embodiment, the stylet includes stainless steel, though other suitable, conductive stylet materials can also be used.

Figure 4:
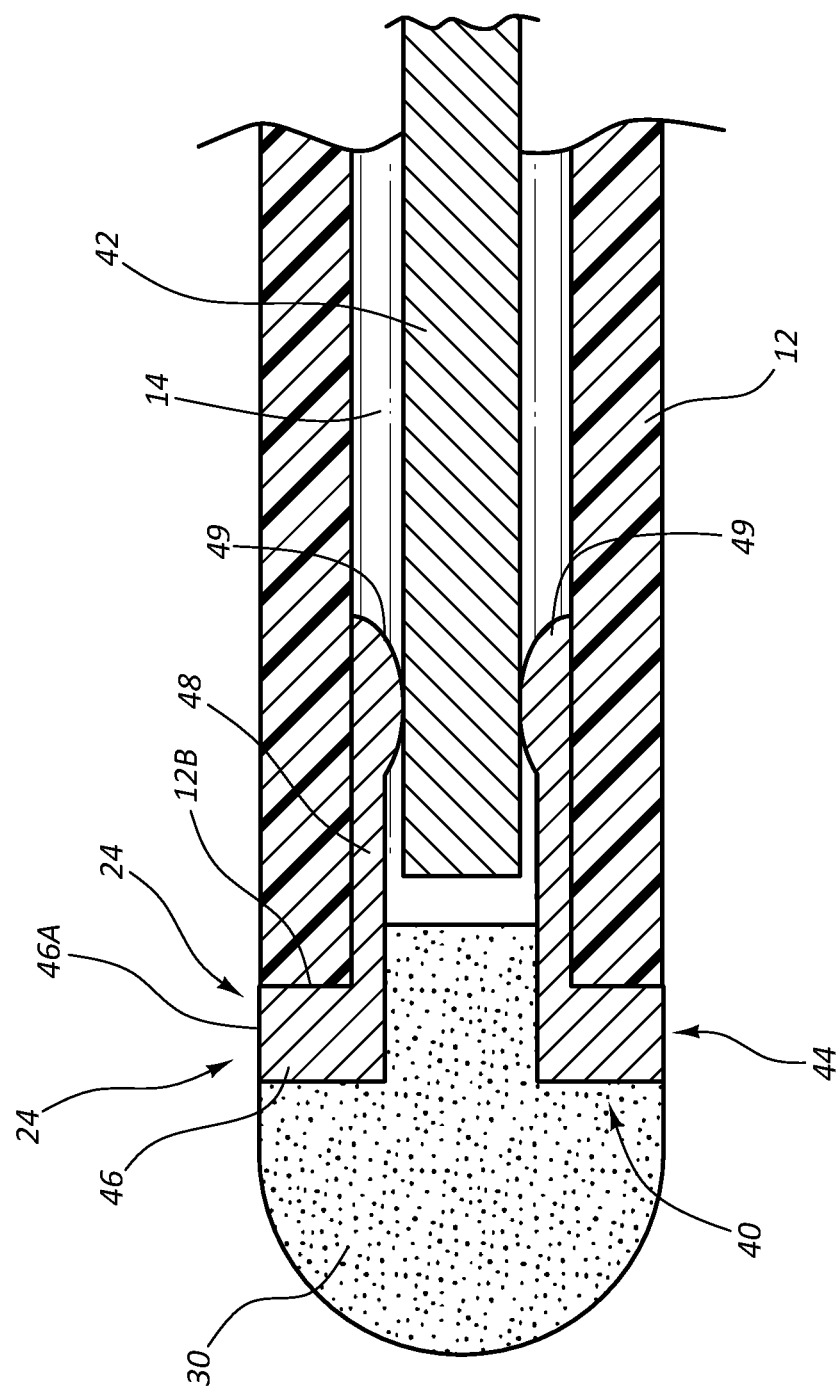
FIG. 4 is a cross sectional view of a distal portion of a catheter tube according to one embodiment.

FIG. 4 shows a distal portion of the catheter 10 including the conductive element 24 to provide an electrically conductive pathway according to another embodiment. As shown, the conductive element 24 includes a conductive insert 44 that is interposed between the plug 30 and the distal end 12B of the catheter tube 12 (though other insert configurations and locations are also possible along the catheter tube). The insert 44 includes a sleeve-shaped outer portion 46 that includes an outer surface 46A that is external to the catheter 10, and a cylindrically-shaped inner portion 48. An inner surface of the cylindrical inner portion 48 includes one or more protuberances 49 so as to facilitate physical coupling of the inner portion with a conductive stylet 42 disposed within the catheter tube lumen 14. In another embodiment, the inner portion 48 can electrically couple with conductive saline or other suitably conductive solution disposed in the lumen. Thus, a conductive pathway is provided through the catheter via the outer portion 46 and the inner portion 48 of the insert 44.

Figure 5:
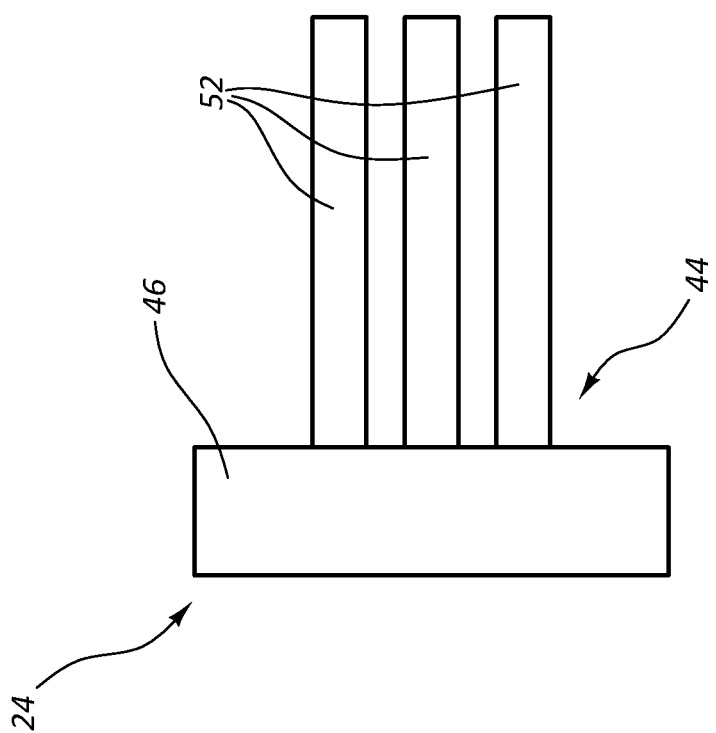
FIG. 5 is a side view of a conductive catheter insert according to one embodiment.

FIG. 5 shows the conductive insert 44 according to another embodiment, wherein the inner portion of the insert includes a plurality of contact arms 52 that can extend proximally within the lumen 14 of the catheter tube 12 (FIG. 5) and are configured to conductively contact the lumen-inserted stylet 42 or conductive liquid disposed therein so as to provide a conductive pathway through the catheter tube 12. It is thus appreciated that both the outer and inner portions of the conductive insert can include one of a variety of configurations.

Figure 6:
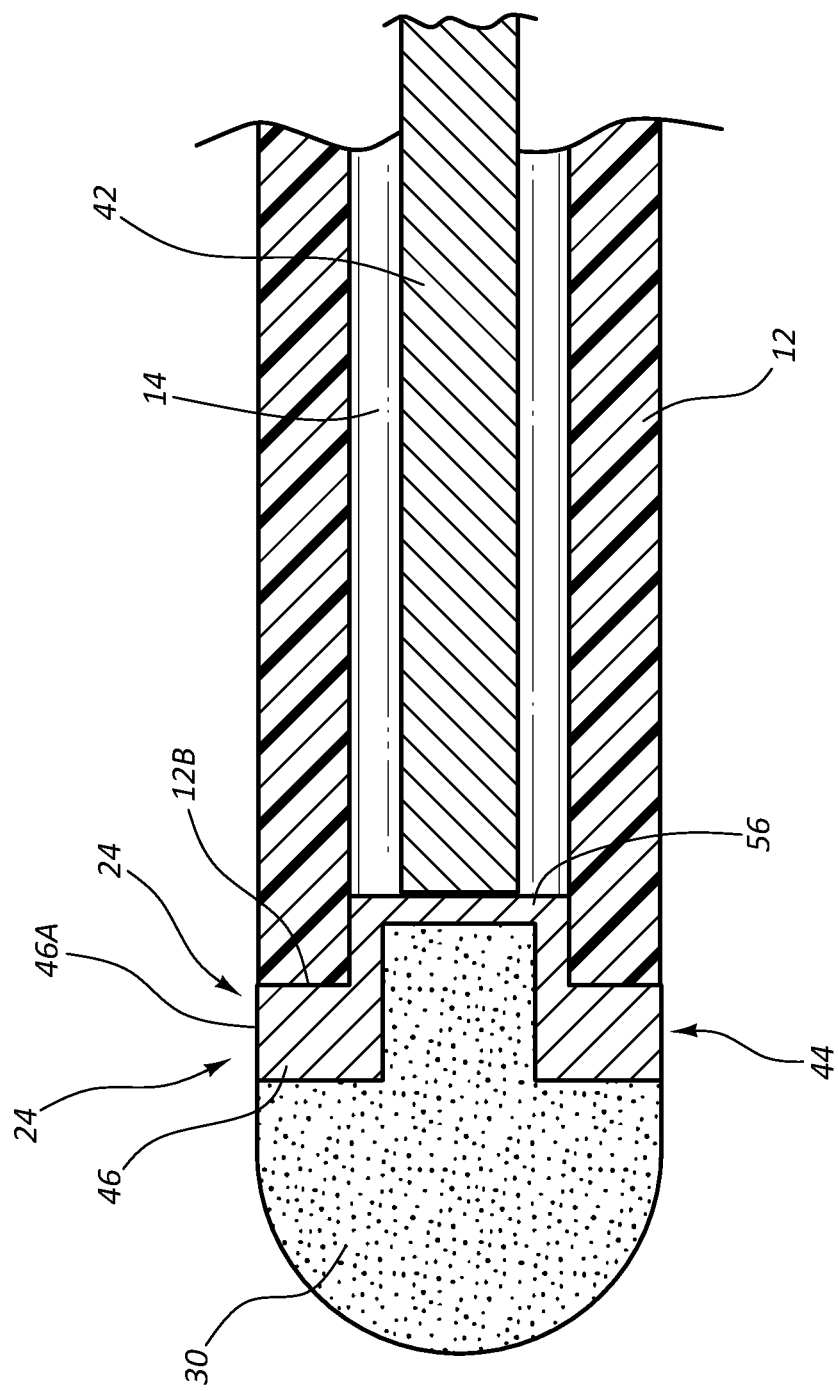
FIG. 6 is a cross sectional view of a distal portion of a catheter tube according to one embodiment.

FIG. 6 shows the conductive insert 44 according to another embodiment, wherein the inner portion of the insert includes a disk 56 that is disposed adjacent a proximal end of the distal plug 30. The disk 56 is configured to conductively contact the lumen-inserted stylet 42 or conductive liquid disposed therein so as to provide a conductive pathway through the catheter tube 12. The thickness, size, shape, etc., of the disk can vary from what is shown and described herein.

Figure 7:
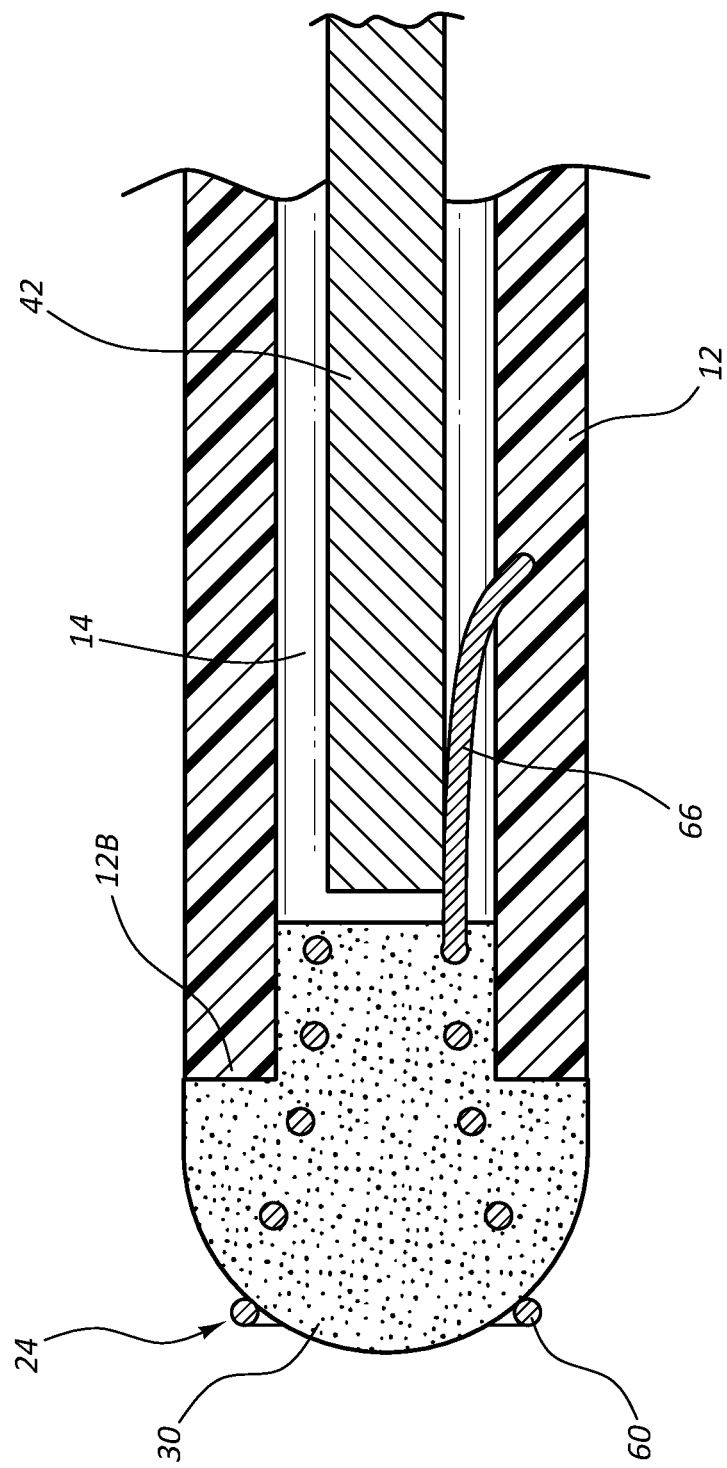
FIG. 7 is a cross sectional view of a distal portion of a catheter tube according to one embodiment.

FIG. 7 shows a distal portion of the catheter 10 including the conductive element 24 to provide an electrically conductive pathway according to another embodiment. As shown, the conductive element 24 includes a conductive coil 60 that is incorporated into the distal plug 30 such that a portion thereof extends to the exterior portion of the catheter proximate the distal end thereof. The coil 60 further includes an inner contact arm 66 that is configured to physically and conductively contact the stylet 42 when disposed in the catheter tube lumen 14 so as to establish a conductive pathway between the exterior of the catheter and the interior of the lumen. Again, and as with other embodiments, a conductive fluid can be disposed in the lumen 14 in addition to or instead of the stylet 42, in one embodiment.

Figure 8:
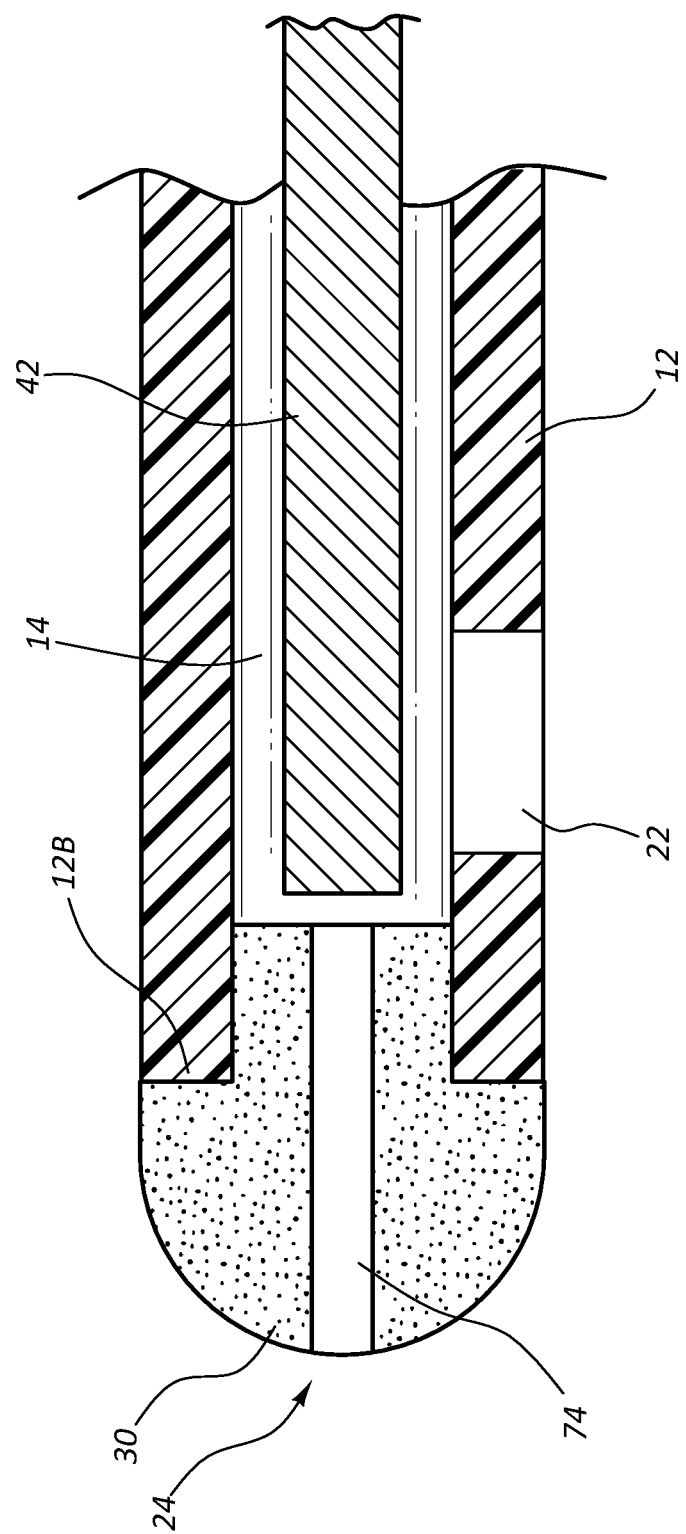
FIG. 8 is a cross sectional view of a distal portion of a catheter tube according to one embodiment.

FIG. 8 shows a distal portion of the catheter 10 including the conductive element 24 to provide an electrically conductive pathway according to another embodiment. As shown, the conductive element 24 includes a conduit 74 defined at time of catheter manufacture longitudinally through the distal plug 30. When initially placed within the patient vasculature, the conduit 74 is open, enabling fluid transfer, and thus electrical signal passage, between the vessel in which the catheter tube is disposed and the catheter tube lumen 14. After a short period of time with the catheter indwelling within the vasculature, the conduit 74 will be filled with thrombus formed by the body, thus thereafter preventing fluid flow therethrough. Thus, the conductive pathway is available during, and for a relatively short time after, catheter tube insertion into the patient vasculature so that ECG signal monitoring or other conductively related activities may occur. Note that the size, location, and configuration of the conduit 74 can vary from what is shown here. Note also that, though the conduit 74 provides an open pathway for a limited time to the lumen 14, the catheter 10 in the present embodiment can still be considered a generally closed catheter due to the fact that the conduit will be occluded by thrombus not long after insertion of the catheter into the patient body. In one embodiment, note that the conduit can be defined in other portions of the catheter tube, such as through the side wall of the catheter tube, in one example.

Note further that FIG. 8 further shows one example of a slit valve 22 and its position with respect to the distal end of the catheter tube 12. It is appreciated that in one embodiment, the valve is disposed proximal to the conductive element, though in other embodiments it may be disposed distal to the conductive element.

Figure 9A:
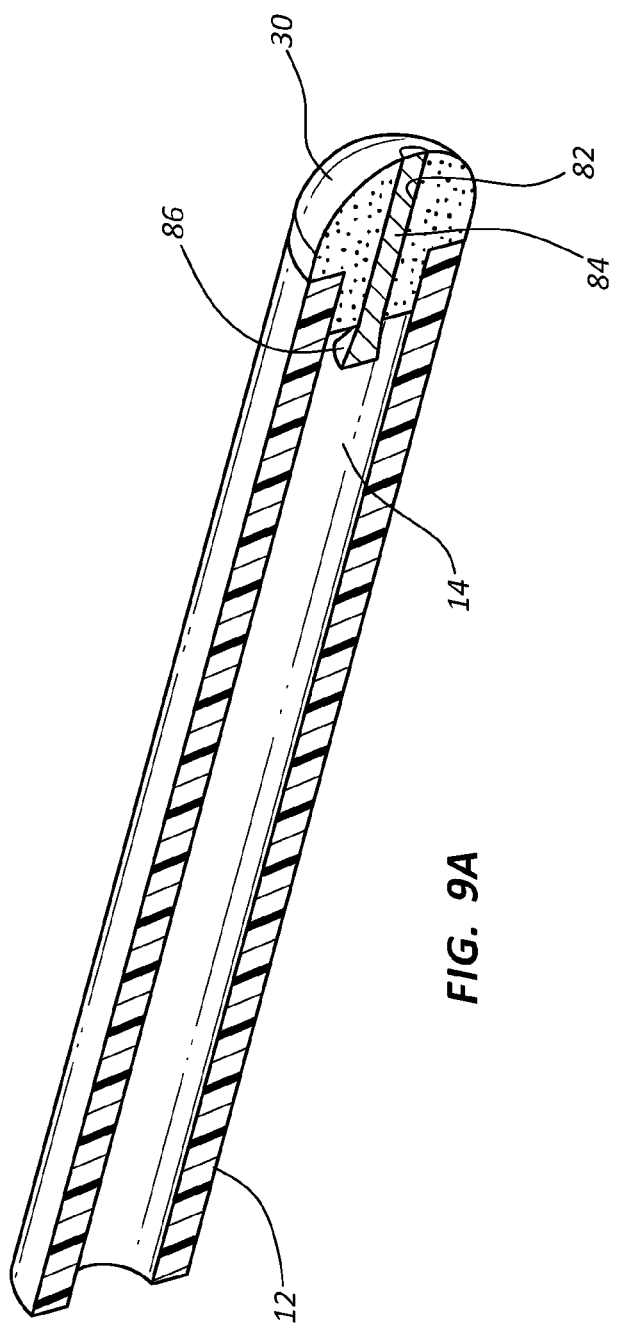
FIGS. 9A-9C are various views of a distal portion of a catheter tube according to one embodiment.
Figure 9B:
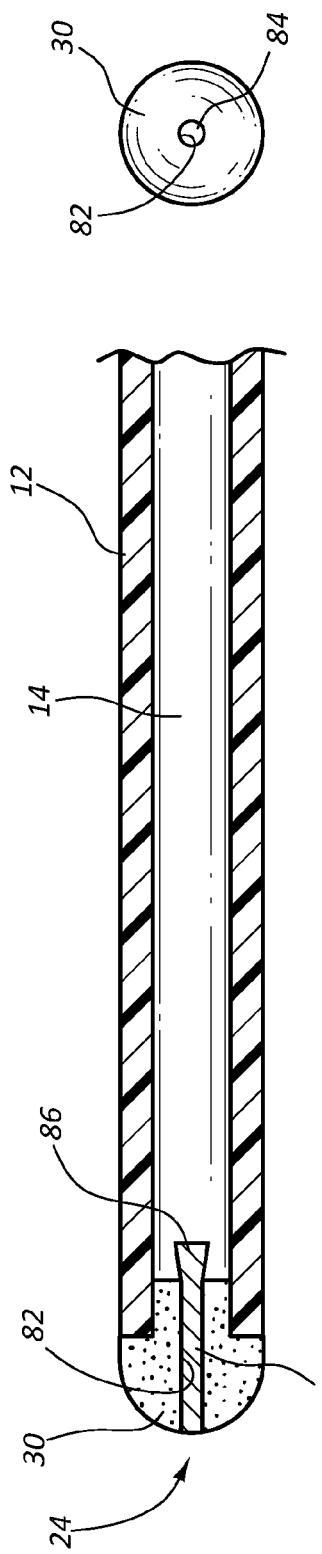
Figure 9C:
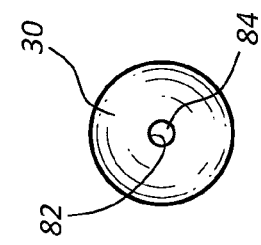

FIGS. 9A-9C show a distal portion of the catheter tube 12 including the conductive element 24 to provide an electrically conductive pathway according to another embodiment. As shown, the conductive element 24 includes a conduit 82 defined at time of catheter manufacture longitudinally through the distal plug 30. A wick 84 is permanently disposed in the conduit 82 such that an extended portion 86 extends proximally into the catheter tube lumen 14 to ensure adequate contact of the wick with the conductive solution disposed within the lumen 14 or with a stylet. So configured, the wick 84 absorbs normal saline or other conductive solution disposed within the lumen 14 such as via capillary action so as to desirably provide a conductive pathway between the lumen and the exterior of the catheter tube 12 via the wick.

The wick 84 in one embodiment includes a suitable material, including wicking yarn, porous fibrous plastic, etc. In one embodiment, the wick material is natively, or treated to be, hydrophilic. In one embodiment, the wick is temporarily disposed in the hole conduit 82 so as to be removable therefrom. In one embodiment, the wick is dissolvable. In yet another embodiment, the wick includes no extended portion. In a further embodiment, the wick extends beyond the distal end of the distal plug 30 during the manufacturing process and can be trimmed so as to be flush with the distal plug surface.

Note that, though the wick 84 enables some fluid transfer from/to the lumen to provide a conductive pathway, the catheter 10 in the present embodiment can still be considered a generally closed catheter due to the fact that the fluid transfer is substantially slow compared to normal fluid transfer via the catheter slit valve.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter assembly for placement in a body of a patient, comprising:
   an elongate catheter tube defining at least one lumen;
   a valve defined in the catheter tube configured to selectively enable fluids to pass therethrough; and
   a conductive element that provides an electrically conductive pathway between the at least one lumen and an exterior of the catheter tube, the conductive element including:
   a wick extending through a closed distal end of the catheter tube from the at least one lumen to an external surface of the catheter tube, the wick capable of wicking up conductive fluid disposed in the at least one lumen.

2. The catheter assembly as defined in claim 1, wherein the wick includes a porous thermoplastic.

3. The catheter assembly as defined in claim 1, wherein the wick includes an extended portion extending proximally into the at least one lumen.

4. The catheter assembly as defined in claim 1, wherein the wick includes a hydrophilic material.

5. The catheter assembly as defined in claim 1, wherein the wick is removably disposed in a conduit in the closed distal end of the catheter tube.

6. The catheter assembly as defined in claim 1, wherein the wick is formed of a dissolvable material.

7. The catheter assembly as defined in claim 1, wherein the wick has a distal end flush with the external surface of the catheter tube.

* * * * *